United States Patent

Takács et al.

Patent Number: 5,218,117
Date of Patent: Jun. 8, 1993

[54] PROCESS FOR PREPARING ISOQUINOLINE COMPOUNDS

[75] Inventors: Kálmán Takács; Iloma Kiss nee Ajzert; István Hermecz; János Ori; Maria H. Pap; Zsolt Bencze; Peter Szekely Kormoczy; Maria Szabo; Judit Szeredy; Csaba Vertesi; Lorand Debreczeni; Jozsef Gaal; Zoltan Kapui, all of Budapest, Hungary

[73] Assignee: Chinoin Gyogyszer Es Vegyeszeti Termekek Gyara Rt., Budapest, Hungary

[21] Appl. No.: 951,448

[22] Filed: Sep. 25, 1992

Related U.S. Application Data

[62] Division of Ser. No. 792,255, Nov. 14, 1991, Pat. No. 5,179,089.

[30] Foreign Application Priority Data

Nov. 14, 1990 [HU] Hungary .................... 7125/90

[51] Int. Cl.⁵ .................... C07D 217/26; C07D 413/12
[52] U.S. Cl. .................... 544/128; 540/497; 544/363; 546/145
[58] Field of Search ............... 540/497; 544/128, 363; 546/145

[56] References Cited

PUBLICATIONS

Harsamyi et al. *Chemical Abstracts*, vol. 82 No. 156, 275x (1975).

Primary Examiner—Robert W. Ramsuer
Attorney, Agent, or Firm—Herbert Dubno; Jonathan Myers

[57] ABSTRACT

The invention relates to novel compounds of the general formula (I),

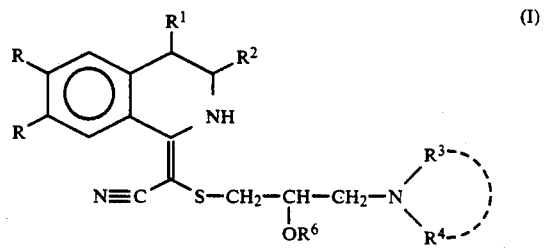

The compounds of the invention antagonize the effects of constrictive mediators, e.g. histamine, acetylcholine or serotonin; they show an antiallergic action and possess an antiinflammatory effect. Thus, these compounds can therapeutically be used as bronchodilators as well as antiallergic or antiinflammatory drugs, particularly in the treatment of bronchial asthma.

2 Claims, No Drawings

PROCESS FOR PREPARING ISOQUINOLINE COMPOUNDS

This is a divisional of co-pending application Ser. No. 07/792,255 filed on Nov. 14, 1991, now U.S. Pat. No. 5,179,089.

FIELD OF THE INVENTION

This invention relates to novel compounds of the formula (I),

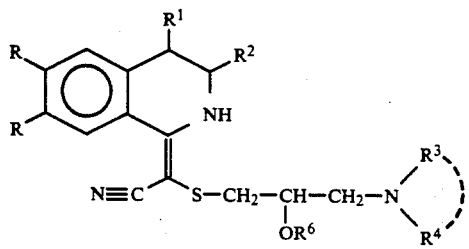

wherein

R means hydrogen or a straight or branched chain $C_{1-6}$alkoxy group;

$R^1$ stands for hydrogen or a straight or branched chain $C_{1-6}$alkyl group;

$R^2$ represents hydrogen or a straight or branched chain $C_{1-6}$alkyl group;

$R^3$ means hydrogen; a straight or branched chain $C_{1-6}$alkyl group optionally substituted by one or two hydroxyl and/or one or two straight or branched chain $C_{1-4}$alkoxy groups; or a $C_{4-7}$cycloalkyl group;

$R^4$ stands for hydrogen or a straight or branched chain $C_{1-6}$alkyl group optionally substituted by one or two hydroxyl and/or one or two straight or branched chain $C_{1-4}$alkoxy groups; or a $C_{4-7}$cycloalkyl group; or $R^3$ and $R^4$ together with the nitrogen atom, to which they are attached form a 4 to 8-membered cyclic group of formula

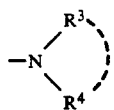

optionally substituted by one or two straight or branched chain $C_{1-4}$alkoxy and/or one or two straight or branched chain $C_{1-4}$alkyl groups, where optionally an oxygen or sulfur atom or an N-$R^5$ group may be substituted for a ring carbon atom, where $R^5$ means hydrogen or a straight or branched chain $C_{1-6}$ aliphatic alkyl group, the 4- to 8-membered cycle optionally being condensed with a benzene ring;

$R^6$ stands for hydrogen or a $C_{1-10}$acyl group and their salts. The invention also relates to the pharmaceutical compositions containing these compounds.

The invention relates also to a process for the preparation of the above new compounds and compositions.

The compounds of formula (I) are unknown in the literature.

R as alkoxy means inter alia a methoxy, ethoxy, propyloxy, isopropyloxy, butoxy, pentoxy or hexyloxy group.

$R^1$ and $R^2$ may stand e.g. for methyl, ethyl, propyl, isopropyl, butyl, isobutyl, tertiary butyl, secondary butyl, pentyl or isopentyl group.

$R^3$ and $R^4$ may mean inter alia the groups defined for $R^1$ or $R^2$ as well as 2-hydroxyethyl or cyclohexyl group.

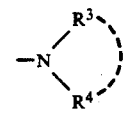

may stand inter alia for a piperidinyl, piperazinyl, 4-methyl-1-piperazinyl, morpholinyl, hexamethylenimino or 1-pyrrolidinyl group.

BACKGROUND OF THE INVENTION $R^6$ may represent e.g. an acetyl or benzoyl group.

The frequency of occurrence of allergic diseases, particularly bronchial asthma is continuously increasing. Social-economical and environmental conditions, enhancement of effectivity of the diagnostics and the lack of an adequate, really healing therapy provide background for this increase. Despite of or partially even due to the elevated drug consumption, the mortality ratio also shows a rising tendency.

Asthma is characterized by an increased sensitivity of the respiratory smooth muscles to the most various stimuli, which leads to a reversible constriction or obstruction of the airways. Chronic asthma eventually results in an irreversible airway obstruction.

Here, an uncontrolled inflammatory process of the respiratory tract appears to be involved. A therapy, which is based only on a bronchodilatation without affecting and even masking the above process represents a merely symptomatic treatment which is essentially harmful and likely contributes to the increase in the mortality.

In opposition to this, an antiinflammatory therapy suppresses the inflammation and at least slows down the harmful background process as well as diminishes the frequency of the demand on a simultaneously used bronchodilatory treatment.

In the cases of drugs being available at present, a further problem appears in the adverse effects decreasing to a high degree their usefulness.

Thus, a most advantageous therapy could be ensured by a drug which is effective against mediator substances causing a spasm of the respiratory smooth muscles and simultaneously possessing antiinflammatory or antiallergic effect without any adverse side effect.

Due to the pathologic nature of bronchial asthma, the effects against the possibly highest number of mediator substances, being constrictive or even inflammatory in character, is very important since the actions of many kinds of endogeneous substances are simultaneously exerted. It would be arbitrary to suppose an outstanding role of any component. Thus, the simultaneous presence of each of the effects defined above is important for these drugs to be developed for the treatment of bronchial asthma.

DESCRIPTION OF THE INVENTION

Now, it has been found during the pharmacological study on the compounds of formula (I) that these substances antagonize the effects of constrictor-type mediators (e.g. histamine, acetylcholine, serotonin), show an antiallergic action and possess an antiinflammatory effect. Thus, the compounds of formula (I) have a bronchodilator-type effect (similarly to the $\beta_2$ antagonists or theophylline) as well as an antiallergic or anti-inflammatory action (similarly to the glucocorticoids, cromolyn or nedocromyl).

Therefore, the compounds of general formula (I) extensively satisfy the therapeutic demands discussed above since they associate the bronchodilatory, antiallergic and antiinflammatory activities with an advantageous lack of toxic and without harmful side effects (without adverse effects).

The invention relates also to a process for the preparation of the new compounds of formula (I), wherein R means hydrogen or a straight or branched chain $C_{1-6}$alkoxy group;

$R^1$ stands for hydrogen or a straight or branched chain $C_{1-6}$alkyl group;

$R^2$ represents hydrogen or a straight or branched chain $C_{1-6}$alkyl group;

$R^3$ means hydrogen; a straight or branched chain $C_{1-6}$alkyl group optionally substituted by one or two hydroxyl and/or one or two straight or branched chain $C_{1-6}$alkoxy groups; or a $C_{4-7}$cycloalkyl group;

$R^4$ stands for hydrogen or a straight or branched chain $C_{1-6}$alkyl group optionally substituted by one or two hydroxyl and/or one or two straight or branched chain $C_{1-4}$alkoxy groups; or a $C_{4-7}$cycloalkyl group, or $R^3$ and $R^4$ together with the nitrogen atom, to which they are attached form a 4 to 8-membered cyclic group of formula $$-N{\overset{R^3}{\underset{R^4}{\diagup\hspace{-0.3em}\diagdown}}}$$

optionally substituted by one or two straight or branched chain $C_{1-4}$alkoxy and/or one or two straight or branched chain $C_{1-4}$alkyl groups, where optionally an oxygen or sulfur atom or an $N-R^5$ group may be substituted for a ring carbon atom, where $R^5$ means hydrogen or a straight or branched chain $C_{1-6}$ aliphatic alkyl group, the 4- to 8-membered cycle optionally being condensed with a benzene ring;

$R^6$ stands for hydrogen or a $C_{1-10}$acyl group
and their salts, which comprises hydrolyzing a compound of the formula (II), $$(II)$$

wherein R, $R^1$ and $R^2$ are as defined above and X means a halide ion, then reacting the obtained derivative of formula (III)

$$(III)$$

wherein R, $R^1$ and $R^2$ are as defined above and Me means a metal atom a) with a racemic or optically active amino alcohol derivative of formula (IV), $$Y-CH_2-CH(OH)-CH_2-N{\overset{R^3}{\underset{R^4}{\diagup\hspace{-0.3em}\diagdown}}} \quad (IV)$$

wherein the $$-N{\overset{R^3}{\underset{R^4}{\diagup\hspace{-0.3em}\diagdown}}}$$

group is as defined above and Y stands for halogen or arylsulfonyl group, or b) with an epoxypropylamine derivative of the formula (V)

$$CH_2{\overset{\diagdown}{\underset{O}{}}}CH-CH_2-N{\overset{R^3}{\underset{R^4}{\diagup\hspace{-0.3em}\diagdown}}} \quad (V)$$

wherein the $$-N{\overset{R^3}{\underset{R^4}{\diagup\hspace{-0.3em}\diagdown}}}$$

group is as defined above, then, if desired, acylating the thus obtained active compounds of formula (I), wherein R, $R^1$, $R^2$, $R^3$, $R^4$ and $R^5$ are as defined above and $R^6$ stands for hydrogen, by known methods to obtain compounds of the formula (I), wherein $R^6$ is as defined above, except hydrogen; or resolving the racemic compounds of formula (I) by known methods; or converting the racemic or optically active compounds of formula (I) to their salts; or liberating the free compounds of formula (I) from their salts.

According to the process of the invention the compounds of formula (II) can be hydrolyzed in aqueous organic solvents, preferably in aqueous aliphatic alcohols by adding a base, suitably an alkaline metal hydroxide. According to a preferred embodiment of this reaction the alkaline metal hydroxide or the aqueous solution thereof is added to the reaction mixture, then the reaction is carried out at the boiling point of the solvent mixture. However, the hydrolysis may be accomplished also under stirring at room temperature since the compounds of formula (II) are hydrolyzed also at lower temperatures.

Although the hydrolysis of compounds of the formula (II) starts even after adding 1 molar equivalent of alkali, this process is rather low, therefore it is suitable to use the alkali in excess. When the compounds of formula (III) are reacted with compounds of the formula (IV) or their salts or with the salts of compounds of the formula (V), the amount of alkali needed to liberate the base from the latter salts may already be added to the reaction mixture during the hydrolysis of the compounds of formula (II). On reacting the thiols of formula (III) with the salts of the compounds of formula (IV) it is suitable to carry out the reaction in the presence of 2 to 6 moles of alkali. The amount of the base used is proportionally diminished when the compounds of formula (IV) or (V) are added in their base form to the reaction mixture.

It is suitable to react the thiols of formula (III), present in solution as their salts after hydrolysis, without isolation with the compounds of formula (IV) or (V). The compounds of formula (IV) or (V) may be added as their solid salts to the reaction mixture. However alternatively, after dissolving the salts of the compounds of formula (IV) or (V) in water or in a mixture of water with a water-miscible organic solvent, preferably an alcohol, their solutions may be added dropwise to the reaction mixture. The addition may be carried out while refluxing the reaction mixture but a lower temperature may also be used. The substances of formula (IV) or (V) can also be employed in their free base form; the addition may be achieved by using or without a solvent.

After adding the compounds of formula (IV) or (V) the reaction mixture is further boiled under a reflux condenser or stirred at a lower temperature, if desired, even under cooling. The compounds of formula (I) formed in the reaction remain in solution in their free base form. After termination of the reaction the products of formula (I) are isolated by using commonly known working up methods. The organic solvent is preferably evaporated under reduced pressure, whereby the product of formula (I) is separated in an oily or crystalline form from the remaining aqueous medium. Any crystalline base of the formula (I) is separated from the mother liquor by filtration whereas the oily crude products are extracted from the aqueous phase. The extraction may be carried out by using water-immiscible solvents, e.g. ethers, hydrocarbons, halogenated hydrocarbons and the like commonly employed for this purpose. After extraction the solutions are dried and the solvent is evaporated under reduced pressure. The evaporation residue is an oily product which becomes crystalline in several cases while standing or by rubbing as both crystalline and oily substances may occur among the bases of formula (I).

The crude products of formula (I) can be purified as crude bases or alternatively, the crude bases may be converted to their salts with mineral or organic acids, and, if desired, the salts obtained may be subjected to a further purification. Methods commonly used in the synthetic organic chemistry such as recrystallization, cromatographical methods and the like can be employed for the purification. Preferred and pharmacologically acceptable salts can be formed by using e.g. hydrochloric acid, hydrobromic acid, hydroiodic acid, sulfuric acid, nitric acid or phosphoric acid as inorganic acids; or citric acid, acetic acid, formic acid, succinic acid, lactic acid, malonic acid, maleic acid, propionic acid, fumaric acid and ascorbic acid as organic acids. Other organic or inorganic acids are also suitable.

A possibility of separation of optically active antipodes comprises forming salts of the compounds of formula (I) with optically active acids and then crystallizing the salts obtained. This method may be accomplished under the usual conditions of resolution by using commonly employed optically active acids such as d-tartaric acid and derivatives thereof, d-camphorsulfonic acid, d-camphoric acid and the like. The salt formation may be carried out in organic solvents or in a mixture thereof. The precipitating crystalline salts are purified by recrystallization from organic solvents, preferably from alcohols (e.g. ethanol, isopropanol). After resolution the optically active bases are liberated by adding an alkali. The salts of the antipodes formed with mineral acids can be obtained by adding mineral acids without liberating the bases; alternatively, these salts may be formed by reacting the optically active bases with mineral acids.

Compounds of the formula (I) containing a $C_{1-10}$ acyl group as $R^6$ are prepared by the acylation of compounds of the formula (I), wherein $R^6$ is hydrogen. The acylation may be performed by using acyl halides or anhydrides, preferably in the presence of organic or inorganic bases in a manner known per se. This reaction may be carried out in a solvent or by using an excess of the acylating agent (e.g. acetic anhydride) as solvent. All solvents being inert to the acylating agents (e.g. hydrocarbons, halohydrocarbons, pyridine) are useful for this purpose. The products are isolated by the usual methods, e.g. evaporation and recrystallization.

The starting substances of formula (II) and the process for their preparation are known from the German patent specification No. 2,426,267.

The compounds of formula (IV) are known and can be prepared according to J. Org. Chem. 25, 1424 (1960). The compounds of formula (V) are also known and are prepared as described in J. Am. Chem. Soc. 80, 1257 (1958).

SPECIFIC EXAMPLES

The pharmacological effects of the compounds according to the invention were investigated by using the methods described hereinafter.

I. Study on the effects against spasmogenic mediators [modified method of J. C. Castillo et al.: Exp. Ther. 90, 104 (1947)]

The investigation on isolated organs were carried out as follows.

OHF Lt/R9 guinea pigs of both sexes weighing 300 to 400 g each were anaesthetized by pentobarbital.

Their trachea was removed and sectioned in the opposite side to the site of smooth muscle in longitudinal direction. Subsequently, a strip-like preparation was obtained by serrately cutting.

The organ was suspended in an organ bath containing 35 ml of Krebs solution at 37° C. bubbled through by carbogen gas (consisting of 95% of oxygen and 5% of carbon dioxide).

A rest load of 0.5 g was used. Several washings were carried out during the incubation period of 30 minutes.

The change in the tension of the tracheal smooth muscle was followed by using an isometric Grass FT-03 type tensiometer sensor device. A washing was made following the cumulative dose series of the given mediator (e.g. histamine). After reaching the base line, by 15 minutes after administration of the given concentration of the inhibitory (antiasthmatic) substance to be tested, the next cumulative dose series of the mediator was administered. In the case of an inhibitory action, the strength of effect, following the second dose series of the mediator, was increased in comparison to that of the first (control) series.

For characterization of strength of the competitive antagonistic effect the $pA_2$ value was determined according to the method of Schield [Br. J. Pharmacol. 4, 277 (1949)]. A $pd'_2$ value was calculated [J. M. Van Rossum: Arch. Int. Pharmacodyn 143, 317 (1963)] to characterize the noncompatitive antagonistic effectivity. The higher the $pA_2$ or $pd'_2$ value, respectively were, the higher was the antagonistic effect.

Theophylline was used as reference drug having the following values:

$pd'_2$ value against histamine: 5.80
$pd'_2$ value against acetylcholine: 6.43
$pd'_2$ value against serotonin: 6.49.

The results obtained in the above test by the compounds of formula (I) of the invention are summarized in Table I.

TABLE I

| Compound of the Example No. | Inhibition of the histamine-induced constriction of isolated tracheal smooth muscle of guinea pig $pd'_2$ |
|---|---|
| 1 | 5.04 |
| 2 | 4.91 |
| 3 | 4.57 |
| 4 | 4.30 |
| 5 | 4.34 |
| 6 | 6.69 |
| 7 | 4.76 |
| 8 | 4.87 |
| 9 | 4.38 |
| 10 | 3.98 |
| 11 | 4.45 |
| 12 | 4.81 |
| 13 | 4.90 |
| 14 | 4.58 |
| 15 | 4.46 |
| 16 | 4.49 |
| 17 | 5.74 |
| 18 | 6.91 |
| 19 | 4.01 |
| 20 | |
| 21 | 5.54 |
| 22 | 5.14 |
| 23 | 4.76 |
| 24 | 5.93 |
| 25 | 6.38 |
| 26 | 5.06 |
| 27 | 6.27 |
| 28 | 6.36 |
| theophylline | 5.80 |

II. Study of the antiallergic effect

1) The effect influencing the active local anaphylactic reaction was measured according to the method of M. Koltay [Arch. Allergy App. Immun. 71, 181 (1983)].

Female OFA rats weighing 160 to 180 g each were sensitized by bovine serum albumin (BSA) adsorbed to 50 μg of $Al(OH)_3$ gel together with the simultaneous administration of Bordatella pertussis vaccine.

The anaphylactic reaction was elicited by injecting 100 μg of BSA into the right hind paw plant in the 14th day.

The measurements were carried out before and 30 minutes after eliciting the reaction. The animals were orally treated with the compound to be tested 1 hour before the injection of BSA. The results were expressed as percentage inhibition compared to the control group (average % ±S.E.M.).

2) The acute antiinflammatory effect was determined by using the carrageenin-induced rat paw edema test [C. A. Winker et al.: Proc. Soc. Exp. Med. 111, 544 (1962)].

Female CFY rats weighing 100 to 120 g each were used after starvation for 24 hours.

The inflammation was induced by injecting 0.1 ml of 1% carrageenin solution into the right hind paw plant.

The severity of inflammation was determined by using an Ugo-Basile type plethysmometer. The measurement was carried out before and 1.5, 3 and 4.5 hours after induction of the inflammation.

The animals were orally treated with the substance to be tested 1 hour before administration of carrageenin. The effect was expressed as percentage inhibition related to the control group.

3) Dextran-induced rat paw edema test

The method of S. Gourvaisier and R. Ducrot [Arch. Int. Pharmacodyn. Ther. 102, 33 (1955)] was employed.

The method described for the carrageenin edema test was followed, except that the measurements were carried out 30, 60, 90, 120 and 180 minutes after induction of the inflammation.

For the use as medicaments, the compounds of formula (I) and their salts are formulated to pharmaceutical compositions such as tablet, dragée, suppository, capsule, solution, powder mixture, injectable or inhalation compositions after adding various additives by methods commonly used in the pharmaceutical industry. Being in general readily soluble in aqueous media, the salts of compounds of the formula (I) are convenient to utilize for the preparation of solutions which can therapeutically be used in both injectable and inhalable compositions.

The reference substances listed hereinafter together with their pharmacological values were utilized in the investigations discussed hereinabove.

1. Inhibition of the spasmogenic mediator-induced constriction of the isolated tracheal smooth muscle of the guinea pig

| | Histamine | Serotonin | Acetylcholine |
|---|---|---|---|
| $pd'_2$ of theophylline | 5.80 | 6.16 | 6.43 |

2. Effect influencing the active local anaphylactic reaction on rat

| Compound | Oral dose mg/kg | Protective effect % in the 30th minute |
|---|---|---|
| Naproxen | 30 | 2.2 |

-continued

| Compound | Oral dose mg/kg | Protective effect % in the 30th minute |
| --- | --- | --- |
| BW 755C | 50 | 52.9 |
| Dexamethasone | 0.5 | 45.5 |

3. Carrageenin-induced rat paw edema

| Compound | Oral dose mg/kg | Protective effect % | | |
| --- | --- | --- | --- | --- |
| | | 1.5 | 3 | 4.5 |
| | | hours | | |
| Naproxen | 20 | 33.2 | 44.3 | 40.4 |

4. Dextran-induced rat paw edema test

| Compound | Oral dose mg/kg | Protective effect % | | | | |
| --- | --- | --- | --- | --- | --- | --- |
| | | 30 | 60 | 90 minutes | 120 | 180 |
| Naproxen | 20 | 16.9 | 20.1 | 18.9 | 23.3 | 21.6 |
| BW-755C | 50 | 15.4 | 12.3 | 17.2 | 7.9 | 11.3 |
| dexamethasone | 0.5 | 42.7 | 36.8 | 51.1 | 52.1 | 45.5 |

The invention is further illustrated in detail by the following non-limiting Examples.

EXAMPLE 1

Preparation of 2-(6,7-dimethoxy-1,2,3,4-tetrahydro-1-isoquinolinylidene)-2-(3-diethylamino-2-hydroxypropyl)mercaptoacetonitrile hydrochloride After dissolving 3.85 g of S-[α-cyano-α-(6,7-dimethoxy-1,2,3,4-tetrahydro-1-isoquinolinylidene)-methyl]isothiuronium bromide (prepared as described in our earlier German patent specification No. 2,426,267) in the mixture of 80 ml of ethanol and 20 ml of water by heating, 16.0 ml of 10% sodium hydroxide solution are added and the reaction mixture is refluxed for 90 minutes, then 1.7 g of 1-chloro-3-diethylamino-2-propanol dissolved in 10 ml of methanol (prepared by reacting diethylamine with epichlorohydrin in methanol according to J. Org. Chem. 25, 1424 (1960)) are added dropwise to the mixture. After refluxing the reaction mixture for 6 hours and then evaporating the organic solvent under reduced pressure, concentrated hydrochloric acid is added dropwise to the remaining aqueous-oily residue until reaching a pH value of 5 to 6. The solution is clarified by activated charcoal, filtered and the filtrate is alkalized by adding 10% sodium hydroxide solution. A yellow oil precipitates which becomes solid by rubbing. After filtration and drying, the product is dissolved in 20 ml of isopropanol and acidified by adding hydrogen chloride in abs. ethanol solution to obtain 1.8 g of the named compound, m.p.: 179° C.

Analysis for $C_{20}H_{30}ClN_3O_3S$ (molecular weight 427.99) calculated: N 9.82; Cl 8.28; S 7.49%; found: N 9.91; Cl 8.40; S 7.50%.

EXAMPLE 2

Preparation of 2-(6,7-diethoxy-1,2,3,4-tetrahydro-1-isoquinolinylidene)-2-(3-diethylamino-2-hydroxypropyl)mercaptoacetonitrile hydrochloride The process described in Example 1 is followed, except that 4.15 g of S-[α-cyano-α-(6,7-diethoxy-1,2,3,4-tetrahydro-1-isoquinolinylidene)-methyl]isothiuronium bromide and 1-chloro-3-diethylamino-2-propanol are used as reactants to give the named compound in a yield of 2.1 g, m.p.: 149° C.

Analysis for $C_{22}H_{34}ClN_3O_3S$ (molecular weight 456.04): calculated: N 9.22; Cl 7.77; S 7.03%; found: N 9.08; Cl 7.93; S 7.31%.

Results of the carrageenin-induced rat paw edema test

| 50 mg/kg (p.o.) Percentage of the protective effect | 1.5 −22.9 | 3 −20.6 | 4.5 hours −11.3 |
| --- | --- | --- | --- |

Inhibition of development of the dextran-induced rat paw edema:

| 50 mg/kg (p.o.) Percentage of inhibition | 30 −24 | 60 −21 | 90 −25 | 120 −23 | 180 minutes −17 |
| --- | --- | --- | --- | --- | --- |

EXAMPLE 3

Preparation of 2-(6,7-dimethoxy-1,2,3,4-tetrahydro-isoquinolinylidene)-2-[3-(N-methyl-N-2-hydroxyethyl)-amino-2-hydroxypropyl]-mercapto-acetonitrile hydrochloride The process described in Example 1 is followed by using 3.85 g of S-[α-cyano-α-(6,7-dimethoxy-1,2,3,4-tetrahydro-1-isoquinolinylidene)methyl]-isothiuronium bromide and 1-chloro-3-(N-methyl-N-2-hydroxyethyl)-amino-2-propanol as starting substances to obtain the named compound in a yield of 2.6 mg, m.p.: 136° C. (from abs. ethanol).

| Analysis for $C_{19}H_{28}ClN_3O_4S$ (molecular weight 429.96) | | | | | |
| --- | --- | --- | --- | --- | --- |
| | C | H | N | Cl | S |
| calculated: | 53.07 | 6.56 | 9.77 | 8.25 | 7.46%; |
| found: | 52.82 | 6.82 | 9.40 | 8.13 | 7.50%. |

EXAMPLE 4

Preparation of 2-(6,7-dimethoxy-1,2,3,4-tetrahydro-1-isoquinolinylidene)-2-[3-(N,N-bis-2-hydroxyethyl)-amino-2-hydroxypropyl]-mercapto-acetonitrile hydrochloride dihydrate The process described in Example 1 is followed by using 3.85 g of S-[α-cyano-α-(6,7-dimethoxy-1,2,3,4-tetrahydro-1-isoquinolinylidene)methyl]-isothiuronium bromide and 1-chloro-3-(N,N-bis-2-hydroxyethyl)-amino-2-propanol as starting substances to obtain the named compound in a yield of 2.3 g, m.p.: 135° C. (from 96% etanol).

| Analysis for $C_{20}H_{34}ClN_3O_7S$ (molecular weight 496.02) | | | | | |
| --- | --- | --- | --- | --- | --- |
| | C | H | N | Cl | S |
| calculated: | 48.43 | 6.91 | 8.47 | 7.15 | 6.46%; |
| found: | 48.66 | 6.77 | 8.25 | 7.45 | 6.31%. |

Results of the carrageenin-induced rat paw edema test

| 50 mg/kg (p.o.) | 1.5 | 3 | 4.5 hours |
|---|---|---|---|
| Percentage of the protective effect | −25.0 | −26.0 | −24.0 |

EXAMPLE 5

Preparation of
2-(6,7-diethoxy-1,2,3,4-tetrahydro-1-isoquinolinylidene)-2-[3-(N,N-bis-2-hydroxyethyl)-amino-2-hydroxypropyl]mercapto-acetonitrile hydrochloride The process described in Example 1 is followed by using 4.15 g of S-[α-cyano-α-(6,7-diethoxy-1,2,3,4-tetrahydro-1-isoquinolinylidene)methyl]-isothiuronium bromide and 1-chloro-3-(N,N-bis-2-hydroxyethyl)-amino-2-propanol as starting substances to obtain the named compound in a yield of 3.1 g, m.p.: 165° C. (from abs. ethanol).

| Analysis for $C_{22}H_{34}ClN_3O_5S$ (molecular weight 488.04) | | | | |
|---|---|---|---|---|
| | C | H | N | Cl | S |
| calculated: | 54.14 | 7.02 | 8.61 | 7.27 | 6.57%; |
| found: | 54.14 | 7.00 | 8.61 | 7.31 | 6.30%. |

Results of the carrageenin-induced rat paw edema test

| 50 mg/kg (p.o.) | 1.5 | 3 | 4.5 hours |
|---|---|---|---|
| Percentage of the protective effect | −21.0 | −16.5 | −10.0 |

EXAMPLE 6

Preparation of
2-(6,7-dimethoxy-1,2,3,4-tetrahydro-1-isoquinolinylidene)-2-(2-hydroxy-3-isopropylamino-propyl)mercaptoacetonitrile hydrochloride hemihydrate The process described in Example 1 is followed, by using 3.85 g of S-[α-cyano-α-(6,7-dimethoxy-1,2,3,4-tetrahydro-1-isoquinolinylidene)methyl]-isothiuronium bromide and 1-chloro-3-isopropylamino-2-propanol as starting substances to give the named compound in a yield of 2.6 g, m.p.: 176° C. (from isopropanol).

| Analysis for $C_{19}H_{28}ClN_3O_3S \cdot 0.5H_2O$ (molecular weight 422.97) | | | | |
|---|---|---|---|---|
| | C | H | N | Cl | S |
| calculated: | 53.95 | 6.91 | 9.94 | 8.38 | 7.58%; |
| found: | 53.60 | 6.69 | 10.24 | 8.47 | 7.60%. |

Results of the carrageenin-induced rat paw edema test

| 50 mg/kg (p.o.) | 1.5 | 3 | 4.5 hours |
|---|---|---|---|
| Percentage of the protective effect | 0 | −17.0 | 0 |

EXAMPLE 7

Preparation of
2-(6,7-diethoxy-1,2,3,4-tetrahydro-1-isoquinolinylidene)-2-(2-hydroxy-3-isopropylamino-propyl)mercaptoacetonitrile hydrochloride The process described in Example 1 is followed, by using 4.15 g of S-[α-cyano-α-(6,7-diethoxy-1,2,3,4-tetrahydro-isoquinolinylidene)methyl]-isothiuronium bromide and 1-chloro-3-isopropylamino-2-propanol as starting substances to obtain the named compound in a yield of 2.8 g, m.p.: 185° C. (from isopropanol).

| Analysis for $C_{21}H_{32}ClN_3O_3S$ (molecular weight 442.01) | | | | |
|---|---|---|---|---|
| | C | H | N | Cl | S |
| calculated: | 57.06 | 7.30 | 9.51 | 8.02 | 7.25%; |
| found: | 56.78 | 7.35 | 9.70 | 8.31 | 7.05%. |

EXAMPLE 8

Preparation of
2-(6,7-dimethoxy-1,2,3,4-tetrahydro-1-isoquinolinylidene)-2-(3-tert-butylamino-2-hydroxy-propyl)mercaptoacetonitrile hydrochloride After adding 80 ml of ethanol and 20 ml of water to 3.85 g of S-[α-cyano-α-(6,7-dimethoxy-1,2,3,4-tetrahydro-1-isoquinolinylidene)methyl]isothiuronium bromide, the mixture is heated until dissolution of the solid material (1 to 2 minutes). After adding 16.0 ml of 10% sodium hydroxide solution, the mixture is refluxed for 90 minutes. Subsequently, 2.02 g of 3-tert-butylamino-1-chloro-2-propanol hydrochloride (prepared by reacting tert-butylamine with epichlorohydrin in methanol as described in the literature cited above, then precipitating the salt from isopropanol solution of the crude base, by adding ethanolic hydrogen chloride solution; m.p. of the hydrochloride: 160° C.) are portionwise added to the reaction mixture which is then refluxed for 5 hours, thereafter ethanol is evaporated under reduced pressure. The residue is the yellow oily crude base, which becomes crystalline while standing, m.p.: 112° C. The crude base is obtained in a yield of 3.6 g.

By adding ethanolic hydrogen chloride solution to an isopropanol solution of the crude base the named hydrochloride is obtained, m.p.: 177° C.

| Analysis for $C_{20}H_{30}ClN_3O_3S$ (molecular weight 427.99) | | | | |
|---|---|---|---|---|
| | C | H | N | Cl | S |
| calculated: | 56.12 | 7.07 | 9.82 | 8.28 | 7.49%; |
| found: | 56.40 | 6.87 | 9.82 | 8.38 | 7.72%. |

EXAMPLE 9

Preparation of
2-(6,7-diethoxy-1,2,3,4-tetrahydro-1-isoquinolinylidene)-2-(3-tert-butylamino-2-hydroxy-propyl)mercaptoaeetonitrile hydrochloride hemihydrate The process described in Example 8 is followed by using 4.15 g of S-[α-cyano-α-(6,7-diethoxy-1,2,3,4-tetrahydro-1-isoquinolinylidene)methyl]isothiuronium bromide and 3-tert-butylamino-1-chloro-2-propanol hydrochloride as starting substances to obtain the named compound in a yield of 2.4 g, m.p.: 160° C. (from isopropanol).

Analysis for $C_{22}H_{34}ClN_3O_3S \cdot 0.5H_2O$ (molecular weight 465.05)

|  | C | H | N | Cl | S |
|---|---|---|---|---|---|
| calculated: | 56.82 | 7.59 | 9.04 | 7.62 | 6.90%; |
| found: | 56.70 | 7.76 | 9.00 | 7.95 | 6.82%. |

EXAMPLE 10

Preparation of
2-(6,7-dimethoxy-1,2,3,4-tetrahydro-1-isoquinolinylidene)-2-(3-cyclohexylamino-2-hydroxypropyl)mercaptoacetonitrile hydrochloride The process described in Example 1 is followed by using 3.85 g of S-[α-cyano-α-(6,7-dimethoxy-1,2,3,4-tetrahydro-1-isoquinolinylidene)-methyl]isothiuronium bromide and 1-chloro-3-cyclohexylamino-2-propanol as starting substances to obtain the named product in a yield of 2.7 g, m.p.: 190° C. (from isopropanol).

Analysis for $C_{22}H_{32}ClN_3O_3S$ (molecular weight 454.02)

|  | C | H | N | Cl | S |
|---|---|---|---|---|---|
| calculated: | 58.20 | 7.10 | 9.26 | 7.81 | 7.06%; |
| found: | 58.00 | 7.40 | 9.02 | 7.81 | 6.86%. |

Results of the carrageenin-induced rat paw edema test

| 50 mg/kg (p.o.) | 1.5 | 3 | 4.5 hours |
|---|---|---|---|
| Percentage of the protective effect | −14.8 | −13.0 | −7.2 |

Inhibition of development of the dextran-induced rat paw edema:

| 50 mg/kg (p.o.) | 30 | 60 | 90 | 120 | 180 minutes |
|---|---|---|---|---|---|
| Percentage of inhibition | −25 | −24 | −25 | −27 | −50 |

EXAMPLE 11

Preparation of
2-(6,7-diethoxy-1,2,3,4-tetrahydro-1-isoquinolinylidene)-2-(3-cyclohexylamino-2-hydroxypropyl)mercaptoacetonitrile hydrochloride The process described in Example 1 is followed by using 4.15 g of S-[α-cyano-α-(6,7-diethoxy-1,2,3,4-tetrahydro-1-isoquinolinylidene)methyl]isothiuronium bromide and 1-chloro-3-cyclohexylamino-2-propanol as starting substances to obtain the named product in a yield of 2.6 g, m.p.: 182° C. (from isopropanol).

Analysis for $C_{24}H_{36}ClN_3O_3S$ (molecular weight 482.08)

|  | C | H | N | Cl | S |
|---|---|---|---|---|---|
| calculated: | 59.79 | 7.53 | 8.72 | 7.36 | 6.65%; |
| found: | 60.02 | 7.50 | 8.65 | 7.16 | 6.45%. |

EXAMPLE 12

Preparation of
2-(6,7-dimethoxy-1,2,3,4-tetrahydro-1-isoquinolinylidene)-2-[2-hydroxy-3-(1-pyrrolidinyl)-propyl]mercaptoacetonitrile hydrochloride hemihydrate The process described in Example 1 is followed by using 3.85 g of S-[α-cyano-α-(6,7-dimethoxy-1,2,3,4-tetrahydro-1-isoquinolinylidene)methyl]isothiuronium bromide and 1-chloro-3-(1-pyrrolidinyl)-2-propanol as starting substances to give 2.1 g of the named product, m.p.: 194° C. (from ethanol).

Analysis for $C_{20}H_{28}ClN_3O_3S \cdot 0.5H_2O$ (molecular weight 434.98)

|  | C | H | N | Cl | S |
|---|---|---|---|---|---|
| calculated: | 55.22 | 6.72 | 9.66 | 8.15 | 7.37%; |
| found: | 55.18 | 7.03 | 9.90 | 8.15 | 7.55%. |

Results of the carrageenin-induced rat paw edema test

| 50 mg/kg (p.o.) | 1.5 | 3 | 4.5 hours |
|---|---|---|---|
| Percentage of the protective effect | −27.2 | −18.9 | −17.6 |

Inhibition of development of the dextran-induced rat paw edema:

| 50 mg/kg (p.o.) | 30 | 60 | 90 | 120 | 180 minutes |
|---|---|---|---|---|---|
| Percentage of inhibition | −20.2 | −15.6 | −14.7 | −14.6 | −12.6 |

EXAMPLE 13

Preparation of
2-(6,7-diethoxy-1,2,3,4-tetrahydro-1-isoquinolinylidene)-2-[2-hydroxy-3-(1-pyrrolidinyl)-propyl]mercaptoacetonitrile hydrochloride The process described in Example 1 is followed by using 4.15 g of S-[α-cyano-α-(6,7-diethoxy-1,2,3,4-tetrahydro-1-isoquinolinylidene)methyl]isothiuronium bromide and 1-chloro-3-(1-pyrrolidinyl)-2-propanol to obtain the named product in a yield of 2.6 g, m.p.: 195° C. (from ethanol).

Analysis for $C_{22}H_{32}ClN_3O_3S$ (molecular weight 454.02)

|  | C | H | N | Cl | S |
|---|---|---|---|---|---|
| calculated: | 58.20 | 7.10 | 9.26 | 7.81 | 7.06%; |
| found: | 57.92 | 7.30 | 9.20 | 7.48 | 6.82%. |

Results of the carrageenin-induced rat paw edema test

| 50 mg/kg (p.o.) | 1.5 | 3 | 4.5 hours |
|---|---|---|---|
| Percentage of the protective effect | −31.8 | −21.8 | −9.05 |

EXAMPLE 14

Preparation of
2-(1,2,3,4-tetrahydro-1-isoquinolinylidene)-2-[2-hydroxy-3-(1-piperidinyl)propyl]mercaptoacetonitrile The process described in Example 8 is followed by using 3.25 g of S-[α-cyano-α-(1,2,3,4-tetrahydro-1-isoquinolinylidene)methyl]isothiuronium bromide and 1-chloro-3-(1-piperidinyl)-2-propanol to give the named product in a yield of 2.1 g, m.p.: 103° C. (from isopropanol).

| Analysis for $C_{19}H_{25}N_3OS$ (molecular weight 343.48) | | | | |
|---|---|---|---|---|
| | C | H | N | S |
| calculated: | 66.43 | 7.34 | 12.23 | 9.34%; |
| found: | 66.17 | 7.14 | 12.50 | 9.24%. |

The hydrochloride of the named product is obtained by adding abs. ethanolic hydrogen chloride solution to the base dissolved in abs. ethanol, m.p.: 187° C.

Inhibition of the active local anaphylactic reaction:
The percentage of inhibition achieved by an oral dose of 50 mg/kg of body weight is −44.1% in the 30th minute after induction of the reaction. Results of the carrageenin-induced rat paw edema test

| 50 mg/kg (p.o.) | 1.5 | 3 | 4.5 hours |
|---|---|---|---|
| Percentage of the protective effect | −20.9 | −20.0 | −20.0 |

EXAMPLE 15

Preparation of
2-(6,7-dimethoxy-1,2,3,4-tetrahydro-1-isoquinolinylidene)-2-[2-hydroxy-3-(1-piperidinyl)-propil]mercaptoacetonitrile hydrochloride After dissolving 3.85 g of S-[α-cyano-α-(6,7-dimethoxy-1,2,3,4-tetrahydro-1-isoquinolinylidene)methyl]isothiuronium bromide in a mixture of 80 ml of ethanol with 20 ml of water under heating, 16 ml of 10% sodium hydroxide solution are added and the reaction mixture is refluxed for 2 hours, then cooled to room temperature and 2.2 g of 1-chloro-3-(1-piperidinyl)-2-propanol hydrochloride are added to the reaction mixture while stirring. The mixture is stirred at room temperature for 2 days and then worked up as described in Example 1. In this way 2.7 g of the named hydrochloride are obtained, m.p.: 210° C. (from ethanol).

| Analysis for $C_{21}H_{30}N_3O_3S$ (molecular weight 440.00) | | | | |
|---|---|---|---|---|
| | C | H | N | S |
| calculated: | 57.32 | 6.87 | 9.55 | 7.29%; |
| found: | 56.99 | 7.01 | 9.32 | 7.43%. |

EXAMPLE 16

Preparation of
2-(1,2,3,4-tetrahydro-1-isoquinolinylidene)-2-[2-hydroxy-3-(4-morpholinyl)propyl]mercaptoacetonitrile hydrochloride hemihydrate The process described in Example 15 is followed by using 3.25 g of S-[α-cyano-α-(1,2,3,4-tetrahydro-1-isoquinolinylidene)methyl]isothiuronium bromide and 1-chloro-3-(4-morpholinyl)-2-propanol hydrochloride as starting substances to obtain 2.7 g of the named product, m.p.: 195° C. (from ethanol).

| Analysis for $C_{18}H_{24}ClN_3O_2S \cdot 0.5H_2O$ (molecular weight 390.93) | | | | |
|---|---|---|---|---|
| | C | H | N | S |
| calculated: | 55.30 | 6.44 | 10.75 | 8.20%; |
| found: | 55.10 | 6.30 | 10.50 | 8.37%. |

Results of the carrageenin-induced rat paw edema test

| 50 mg/kg (p.o.) | 1.5 | 3 | 4.5 hours |
|---|---|---|---|
| Percentage of the protective effect | −29.3 | −22.2 | −20.0 |

EXAMPLE 17

Preparation of
2-(6,7-dimethoxy-1,2,3,4-tetrahydro-1-isoquinolinylidene)-2-[2-hydroxy-3-(4-morpholinyl)-propyl]mercaptoacetonitrile hydrochloride The process described in Example 15 is followed by using 3.85 g of S-[α-cyano-α-(6,7-dimethoxy-1,2,3,4-tetrahydro-1-isoquinolinylidene)methyl]isothiuronium bromide and 1-chloro-3-(4-morpholinyl)-2-propanol hydrochloride as starting materials to obtain the named compound in a yield of 3.3 g, m.p.: 210° C. (from ethanol).

| Analysis for $C_{20}H_{28}ClN_3O_4S$ (molecular weight 441.97) | | | | | |
|---|---|---|---|---|---|
| | C | H | N | Cl | S |
| calculated: | 54.35 | 6.39 | 9.51 | 8.02 | 7.26; |
| found: | 54.42 | 6.52 | 9.63 | 8.00 | 7.54; |

Inhibition of the active local anaphylactic reaction:
The percentage of inhibition achieved by an oral dose of 50 mg/kg is −53.4% in the 30th minute following induction of the reaction.

Results of the carrageenin-induced rat paw edema test

| 50 mg/kg (p.o.) | 1.5 | 3 | 4.5 hours |
|---|---|---|---|
| Percentage of the protective effect | −4.2 | 0 | 0 |

Inhibition of development of the dextran-induced rat paw edema:

| 50 mg/kg (p.o.) | 30 | 60 | 90 | 120 | 180 minutes |
|---|---|---|---|---|---|
| Percentage of inhibition | 27.5 | 32.5 | 32.1 | 32.4 | 20.3 |

EXAMPLE 18

Preparation of
2-(6,7-diethoxy-1,2,3,4-tetrahydro-1-isoquinolinylidene)-2-[2-hydroxy-3-(4-morpholinyl)propyl]mercaptoacetonitrile After adding 80 ml of methanol and 20 ml of water to 4.15 g of S-[α-cyano-α-(6,7-diethoxy-1,2,3,4-tetrahydro-1-isoquinolinylidene)methyl]isothiuronium bromide, the reaction mixture is heated until complete dissolution (1 to 2 minutes). After adding 11.0 ml of 10% sodium hydroxide solution the mixture is refluxed for 90 minutes. After addition of 2.2 g of 1-chloro-3-(4-morpholinyl)-2-propanol hydrochloride, the reaction mixture is refluxed for 5 hours. Then, methanol is evaporated and the residue is cooled down, whereby the crude base crystallizes out to give the named product in a yield of 3.2 g, m.p.: 97° C. (from abs. ethanol).

| Analysis for $C_{22}H_{31}N_3O_4S$ (molecular weight 433.56) | | | | |
|---|---|---|---|---|
| | C | H | N | S |
| calculated: | 60.94 | 7.21 | 9.69 | 7.40%; |
| found: | 60.72 | 7.40 | 9.51 | 7.17%. |

The hydrochloride of the above base is precipitated by adding an ethanolic solution of hydrogen chloride to an abs. ethanolic solution of the base, m.p.: 203° C. (from ethanol).

$LD_{50}$ i.v.
91.37 mg/kg on male rat
132.98 mg/kg on female rat
165.76 mg/kg on male mouse
150.00 mg/kg on female mouse.
$LD_{50}$ p.o.
1204.59 mg/kg on male mouse
1034.65 mg/kg on female mouse.

Inhibition of the active topic anaphylactic reaction

The percentage of inhibition achieved by an oral dose of 50 mg/kg is −31% in the 30th minute following the induction of reaction.

Results of the carrageenin-induced rat paw edema test

| 50 mg/kg (p.o.) | 1.5 | 3 | 4.5 hours |
|---|---|---|---|
| Percentage of the protective effect | −35.8 | −29.3 | −28.4 |

Inhibition of development of the dextran-induced rat paw edema:

| 50 mg/kg (p.o.) | 30 | 60 | 90 | 120 | 180 minutes |
|---|---|---|---|---|---|
| Percentage of inhibition | 29.8 | 38.7 | 30.4 | 26.3 | 28.4 |

EXAMPLE 19

Preparation of
2-(6,7-dimethoxy-1,2,3,4-tetrahydro-1-isoquinolinylidene)-2-(3-hexamethylenimino-2-hydroxypropyl)mercaptoacetonitrile The process described in Example 1 is followed by using 3.85 g of S-[α-cyano-α-(6,7-dimethoxy-1,2,3,4-tetrahydro-1-isoquinolinylidene)methyl]isothiuronium bromide and 1-chloro-3-hexamethylenimino-2-propanol as starting materials to obtain 1.7 g of the named base as a yellow oil.

The hydrochloride of the above base is precipitated from ethanolic solution. The hydrochloride crystallizes with 1 mole of crystal ethanol and half mole of crystal water, m.p.: 110° to 112° C. (from ethanol).

| Analysis for $C_{22}H_{31}N_3O_3S.HCl.C_2H_5OH.0.5H_2O$ (molecular weight 509.10) | | | | | |
|---|---|---|---|---|---|
| | C | H | N | Cl | S |
| calculated: | 56.62 | 7.72 | 8.25 | 6.96 | 6.30%; |
| found: | 56.66 | 8.05 | 8.20 | 6.70 | 6.65%. |

Results of the carrageenin-induced rat paw edema test

| 50 mg/kg (p.o.) | 1.5 | 3 | 4.5 hours |
|---|---|---|---|
| Percentage of the protective effect | −29.0 | −24.2 | −19.5 |

Inhibition of development of the dextran-induced rat paw edema:

| 50 mg/kg (p.o.) | 30 | 60 | 90 | 120 | 180 minutes |
|---|---|---|---|---|---|
| Percentage of inhibition | −28.2 | −26.6 | −27.3 | −27.8 | −22.8 |

EXAMPLE 20

2-(6,7-dimethoxy-1,2,3,4-tetrahydro-1-isoquinolinylidene)-2-[2-hydroxy-3-(1,2,3,4-tetrahydro-2-isoquinolinyl)propyl]mercaptoacetonitrile hydrochloride hydrate The process described in Example 15 is followed by using 3.85 g of S-[α-cyano-α-(6,7-dimethoxy-1,2,3,4-tetrahydro-1-isoquinolinylidene)methyl]isothiuronium bromide and 1-chloro-3-(1,2,3,4-tetrahydro-2-isoquinolinyl)-2-propanol as starting materials to yield 3.1 g of named product, m.p.: 140° C. (from ethanol).

| Analysis for $C_{22}H_{30}ClN_3O_3S.H_2O$ (molecular weight 506.05) | | | | |
|---|---|---|---|---|
| | C | H | N | Cl |
| calculated: | 59.33 | 6.37 | 8.30 | 7.01%; |
| found: | 59.29 | 6.38 | 7.96 | 7.03%. |

EXAMPLE 21

Preparation of
2-(6,7-dimethoxy-1,2,3,4-tetrahydro-1-isoquinolinylidene)-2-[2-hydroxy-3-(4-methyl-1-piperazinyl)propyl]mercaptoacetonitrile hydrochloride The process described in Example 1 is followed by using 3.85 g of S-[α-cyano-α-(6,7-dimethoxy-1,2,3,4-tetrahydro-1-isoquinolinylidene)methyl]isothiuronium bromide and 1-chloro-3-(4-methyl-1-piperazinyl)-2-propanol as starting materials to give the named product in a yield of 1.7 g, m.p.: 243° C. (from 90% ethanol).

| Analysis for $C_{21}H_{32}Cl_2N_4O_3S$ (molecular weight 491.48) | | | | |
|---|---|---|---|---|
| | C | H | N | S |
| calculated: | 51.32 | 6.56 | 11.40 | 6.52%; |
| found: | 51.35 | 6.61 | 11.24 | 6.57%. |

EXAMPLE 22

Preparation of
2-(6,7-diethoxy-1,2,3,4-tetrahydro-1-isoquinolinylidene)-2-[2-hydroxy-3-(4-methylpiperazinyl)propyl]mercaptoacetonitrile hydrochloride The process described in Example 1 is followed by using 4.15 g of S-[α-cyano-α-(6,7-diethoxy-1,2,3,4-tetrahydro-1-isoquinolinylidene)methyl]isothiuronium bromide and 1-chloro-3-(4-methyl-1-piperazinyl)-2-propanol as starting substances to yield 1.8 g of the named hydrochloride, which crystallizes with 2.5 moles of crystal water from 96% ethanol, m.p.: 220° C.

| Analysis for $C_{23}H_{36}Cl_2N_4O_3S \cdot 2.5H_2O$ (molecular weight 564.57) | | | | |
|---|---|---|---|---|
| | C | H | N | S |
| calculated: | 48.93 | 7.32 | 9.92 | 5.68%; |
| found: | 48.96 | 7.05 | 10.15 | 6.05%. |

EXAMPLE 23

Preparation of
2-(6,7-dimethoxy-1,2,3,4-tetrahydro-1-isoquinolinylidene)-2-[2-acetoxy-3-(4-morpholinyl)propyl]mercaptoacetonitrile hydrochloride After adding 80 ml of benzene and 32 ml of acetic acid anhydride to 4.8 g of 2-(6,7-dimethoxy-1,2,3,4-tetrahydro-1-isoquinolinylidene)-2-[2-hydroxy-3-(4-morpholinyl)propyl]mercaptoacetonitrile, the reaction mixture is refluxed for 2 hours, then evaporated to dryness under reduced pressure. The residue is dissolved in isopropanol and acidified by adding abs. ethanolic hydrogen chloride solution to give the title hydrochloride in a yield of 4.72 g, m.p.: 204° C. (from abs. ethanol).

| Analysis for $C_{22}H_{30}ClN_3O_5S$ (molecular weight 484.01) | | | | | |
|---|---|---|---|---|---|
| | C | H | N | Cl | S |
| calculated: | 54.59 | 6.25 | 8.68 | 7.33 | 6.63%; |
| found: | 54.37 | 6.16 | 8.90 | 7.41 | 6.39%. |

Results of the carrageenin-induced rat paw edema test

| 50 mg/kg (p.o.) | 1.5 | 3 | 4.5 hours |
|---|---|---|---|
| Percentage of the protective effect | −33.8 | −30.9 | −29.5 |

EXAMPLE 24

Preparation of
2-(6,7-diethoxy-1,2,3,4-tetrahydro-1-isoquinolinylidene)-2-[2-acetoxy-3-(4-morpholinyl)propyl]mercaptoacetonitrile After adding 50 ml of benzene and 20 ml of acetic acid anhydride to 3.0 g of 2-(6,7-diethoxy-1,2,3,4-tetrahydro-1-isoquinolinylidene)-2-[2-hydroxy-3-(4-morpholinyl)propyl]mercaptoacetonitrile, the reaction mixture is refluxed for 1 hour, then evaporated to dryness under reduced pressure. After addition of ether, the residue crystallizes out to give the named product in a yield of 2.47 g, m.p.: 133° C. (from isopropanol).

Analysis for $C_{24}H_{33}N_3O_5$ (molecular weight 475.59): calculated: N 8.84; S 6.74%; found: N 8.71; S 6.66%.

Inhibition of the constrictive action of acetylcholine: pd′$_2$: 5.02.

Inhibition of the constrictive action of serotonin: pd′$_2$: 5.05.

Results of the carrageenin-induced rat paw edema test

| 50 mg/kg (p.o.) | 1.5 | 3 | 4.5 hours |
|---|---|---|---|
| Percentage of the protective effect | −25.8 | −20.3 | −20.0 |

EXAMPLE 25

Preparation of
2-(6,7-dimethoxy-1,2,3,4-tetrahydro-1-isoquinolinylidene)-2-[2-benzoyloxy-3-(4-morpholinyl)propyl]mercaptoacetonitrile After adding 40 ml of benzene, 1.0 g of triethylamine and 1.5 g of benzoyl chloride to 4.06 g of 2-(6,7-diethoxy-1,2,3,4-tetrahydro-1-isoquinolinylidene)-2-[2-hydroxy-3-(4-morpholinyl)propyl]mercaptoacetonitrile, the reaction mixture is refluxed for 45 minutes, then cooled down and filtered. After evaporating the filtrate, the residue crystallizes out on adding ethyl acetate to obtain the named product in a yield of 3.25 g, m.p.: 144° C. (from isopropanol).

| Analysis for $C_{27}H_{31}N_3O_5S$ (molecular weight 509.61) | | | | |
|---|---|---|---|---|
| | C | H | N | S |
| calculated: | 63.63 | 6.13 | 8.25 | 6.29%; |
| found: | 64.03 | 6.37 | 8.58 | 6.37%. |

Inhibition of the constrictive action of acetylcholine: pd′$_2$: 4.81.

Results of the carrageenin-induced rat paw edema test

| 50 mg/kg (p.o.) | 1.5 | 3 | 4.5 hours |
|---|---|---|---|
| Percentage of the protective effect | −26.6 | −17.7 | −16.0 |

EXAMPLE 26

Preparation of
2-(6,7-diethoxy-1,2,3,4-tetrahydro-1-isoquinolinylidene)-2-[2-benzoyloxy-3-(4-morpholinyl)propyl]mercaptoacetonitrile hydrochloride 40 ml of benzene, 1.0 g of triethylamine and 1.5 g of benzoyl chloride are added to 4.34 g of 2-(6,7-diethoxy-1,2,3,4-tetrahydro-1-isoquinolinylidene)-2-[2-hydroxy-3-(4-morpholinyl)propyl]mercaptoacetonitrile and the reaction mixture is refluxed for 45 minutes, then cooled down. After filtering and evaporating the solvent under reduced pressure, the residue is dissolved in isopropanol and acidified by adding abs. ethanolic hydrogen chloride solution. In this way 3.77 g of the named hydrochloride crystallize out, m.p.: 207° C. (from ethanol).

| Analysis for $C_{29}H_{36}ClN_3O_5S$ (molecular weight 574.13) | | | | | |
|---|---|---|---|---|---|
| | C | H | N | Cl | S |
| calculated: | 60.66 | 6.32 | 7.32 | 6.18 | 5.59%; |
| found: | 60.80 | 6.37 | 7.22 | 6.24 | 5.88%. |

Inhibition of the constrictive action of acetylcholine: pd'₂: 4.81.

EXAMPLE 27

Preparation of (−)-2-(6,7-diethoxy-1,2,3,4-tetrahydro-1-isoquinolinylidene)-2-[2-hydroxy-3-(4-morpholinyl)-propyl]mercaptoacetonitrile d-camphorsulfonate The mixture containing 8.0 g of 2-(6,7-diethoxy-1,2,3,4-tetrahydro-1-isoquinolinylidene)-2-[2-hydroxy-3-(4-morpholinyl)propyl]mercaptoaceetonitrile and 3.9 g of d-camphorsulfonic acid in 50 ml of abs. ethanol is heated until dissolution of the solid material (a few minutes). After cooling down the crystalline precipitate is filtered and recrystallized from 40 ml of hot abs. ethanol to give 5.0 g of the named salt, m.p.: 172° C.

The base is liberated by adding sodium hydroxide to an aqueous solution of the camphorsulfonate salt. The base melts at 97° C., $[\alpha] = -11.3°$ (c=1, chloroform).

The hydrochloride of the product can be precipitated from anhydrous ethanolic solution by adding anhydrous ethanolic hydrogen chloride solution.

EXAMPLE 28 a) Preparation of (+)-2-(6,7-diethoxy-1,2,3,4-tetrahydro-1-isoquinolinylidene)-2-[2-hydroxy-3-(4-morpholinyl)propyl]mercaptoacetonitrile hydrochloride The ethanolic mother liquor of the salt separation described in Example 27 is evaporated to dryness under reduced pressure and water is added to the residue. After alkalizing the solution obtained by 10% sodium hydroxide solution, the separated oily yellow material is extracted into chloroform. After drying the chloroform solution over anhydrous sodium sulfate and evaporating the solvent under reduced pressure, the residue is dissolved in abs. ethanol and acidified by adding ethanolic hydrogen chloride solution. The named hydrochloride is obtained in a yield of 2.65 g, m.p.: 201° C. (from abs. ethanol), $[\alpha] = 7.7°$ (c=1, water).

b) Preparation of (+)-2-(6,7-diethoxy-1,2,3,4-tetrahydro-1-isoquinolinylidene)-2-[2-hydroxy-3-(4-morpholinyl)propyl]mercaptoacetonitrile 1-camphorsulfonate The process described in Example 27 is followed by using 8.0 g of 2-(6,7-diethoxy-1,2,3,4-tetrahydro-1-isoquinolinylidene)-2-[2-hydroxy-3-(4-morpholinyl)-propyl]mercaptoacetonitrile and 3.9 g of 1-camphorsulfonic acid as starting substances to obtain 5.2 g of the named camphor-sulfonate salt, m.p.: 169°-170° C. (from abs. ethanol).

EXAMPLE 29

Preparation of 2-(6,7-dimethoxy-1,2,3,4-tetrahydro-1-isoquinolinylidene)-2-[2-hydroxy-3-(4-morpholinyl)-propyl]mercaptoacetonitrile hydrochloride After adding 4 ml of 10% sodium hydroxide solution and 6 ml of ethanol to 0.48 g of 2-(6,7-dimethoxy-1,2,3,4-tetrahydro-1-isoquinolinylidene)-2-[2-acetoxy-3-(4-morpholinyl)propyl]mercaptoacetonitrile hydrochloride (product of Example 23), the reaction mixture is refluxed for 30 minutes, then ethanol is evaporated under reduced pressure. The oily residue crystallizes out, it is filtered, washed with water and dried. The product obtained is dissolved in 5 ml of abs. ethanol under heating and the solution is acidified by abs. ethanolic hydrogen chloride solution to give 0.4 g of the named hydrochloride which is identical to the product of Example 17, m.p.: 210° C.

EXAMPLE 30

Preparation of 2-(6,7-diethoxy-1,2,3,4-tetrahydro-1-isoquinolinylidene)-2-[2-hydroxy-3-(4-morpholinyl)-propyl]mercaptoacetonitrile hydrochloride After adding 4 ml of 10% sodium hydroxide solution and 6 ml of ethanol to 0.48 g of 2-(6,7-diethoxy-1,2,3,4-tetrahydro-1-isoquinolinylidene)-2-[2-acetoxy-3-(4-morpholinyl)propyl]mercaptoacetonitrile (product of Example 24), the reaction mixture is refluxed for 30 minutes. After evaporation of the solvent, the residue is extracted with chloroform. The organic solution is dried over anhydrous sodium sulfate. After evaporating the solvent, the residue is dissolved in 5 ml of anhydrous ethanol under heating and acidified by abs. ethanolic hydrogen chloride solution to obtain 0.38 g of the named hydrochloride, which is identical to the product of Example 18, m.p.: 203° C.

EXAMPLE 31

Preparation of 2-(6,7-dimethoxy-1,2,3,4-tetrahydro-1-isoquinolinylidene)-2-[2-hydroxy-3-(1-piperidinyl)-propyl]mercaptoacetonitrile hydrochloride After dissolving 3.85 g of S-[α-cyano-α-(6,7-dimethoxy-1,2,3,4-tetrahydro-1-isoquinolinylidene)methyl]isothiuronium bromide in the mixture of 80 ml of methanol and 20 ml of water, 11.0 ml of 10% sodium hydroxide solution are added, the reaction mixture is refluxed for 2 hours and a solution containing 1.44 g of 1,2-epoxy-3-(1-piperidinyl)propane [prepared as described in J. Am. Chem. Soc. 80, 1257 (1958)] dissolved in 5 ml of methanol is added dropwise to the hot solution. The reaction mixture is refluxed for additional 5 hours. After evaporating methanol under reduced pressure the reaction mixture is worked up as described in Example 1 to obtain 2.3 g of the named hydrochloride which is identical to the product of Example 15, m.p.: 210° C. (from anhydrous ethanol).

EXAMPLE 32

Preparation of 2-(6,7-diethoxy-1,2,3,4-tetrahydro-1-isoquinolinylidene)-2-[2-hydroxy-3-(1-piperidinyl)-propyl]mercaptoacetonitrile hydrochloride The process described in Example 31 is followed by using 4.15 g of S-[α-cyano-α-(6,7-diethoxy-1,2,3,4-tetrahydro-1-isoquinolinylidene)methyl]isothiuronium bromide and 1.41 g of 1,2-epoxy-3-(1-piperidinyl)propane to give 2.6 g of the named hydrochloride, m.p.: 192° C.

We claim:

1. A process for the preparation of a racemic or optically active compound of the formula (I)

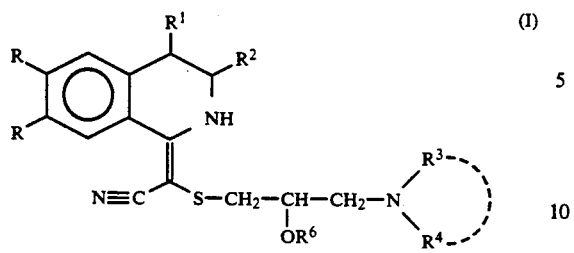

(I)

wherein
- R means hydrogen or a straight or branched chain $C_{1-6}$ alkoxy group;
- $R^1$ stands for hydrogen or a straight or branched chain $C_{1-6}$ alkyl group;
- $R^2$ represents hydrogen or a straight or branched chain $C_{1-6}$ alkyl group;
- $R^3$ means hydrogen; a straight or branched chain $C_{1-6}$ alkyl group optionally substituted by one or two hydroxyl and/or one or two straight or branched chain $C_{1-4}$ alkoxy group(s); or a $C_{4-7}$ cycloalkyl group;
- $R^4$ stands for hydrogen or a straight or branched chain $C_{1-6}$ alkyl group optionally substituted by one or two hydroxyl and/or one or two straight or branched chain $C_{1-4}$ alkoxy group(s); or a $C_{4-7}$ cycloalkyl group; and $R^3$ and $R^4$ together with the nitrogen atom, to which they are attached form a 4 to 8-membered cyclic group of formula

optionally substituted by one or two straight or branched chain $C_{1-4}$ alkoxy and/or one or two straight or branched chain $C_{1-4}$ alkyl group(s), where optionally an oxygen or sulfur atom or an N-$R^5$ group may be substituted for a ring carbon atom, where $R^5$ means hydrogen or a straight or branched chain $C_{1-6}$ aliphatic alkyl group, the 4- to 8-membered cycle optionally being condensed with a benzene ring;
- $R^6$ stands for hydrogen or a $C_{1-10}$ acyl group and the salts thereof as well as hydrates of the free compounds of formula (I) and the salts thereof, which comprises hydrolyzing a compound of the formula (II),

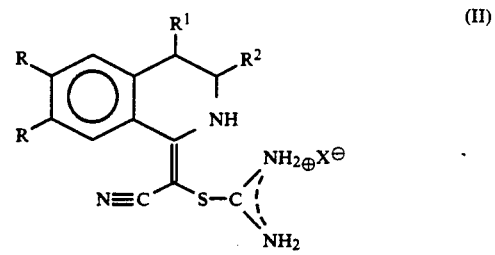

wherein X is a halide ion, then reacting the obtained salt of the formula (III)

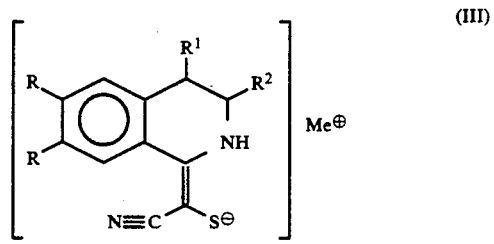

wherein Me is a metal atom
a) with a racemic or optically active compound of the formula (IV),

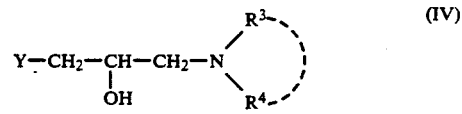

wherein Y is halogen or arylsulfonyl, or with a compound of the formula (V)

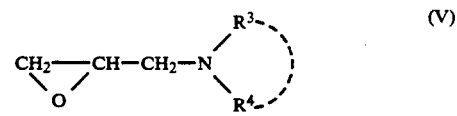

then, if desired, acylating the thus obtained active compounds of the formula (I), wherein $R^6$ stands for hydrogen, to obtain compounds of the formula (I), wherein $R^6$ is as defined above, except hydrogen; or resolving the racemic compounds of formula (I); or converting the racemic or optically active compounds of formula (I) to their salts; or liberating the free compounds of formula (I) from their salts; or liberating the free racemic or optically active compounds of formula (I) from their salts.

2. A process as claimed in claim 1, which comprises reacting the compounds of formula (III) without isolating them with the compounds of formula (IV) or (V), respectively.

* * * * *